US010288559B2

(12) United States Patent
Muniraju et al.

(10) Patent No.: US 10,288,559 B2
(45) Date of Patent: May 14, 2019

(54) GAS CONCENTRATION SENSOR WITH IMPROVED ACCURACY

(71) Applicant: HONEYWELL INTERNATIONAL INC., Morris Plains, NJ (US)

(72) Inventors: Raghavendra Muniraju, Bangalore (IN); Mahadevanna Basavaraj Shreshthi, Bangalore (IN); Venkata Subbanna Karanam, Bangalore (IN)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 141 days.

(21) Appl. No.: 15/449,107

(22) Filed: Mar. 3, 2017

(65) Prior Publication Data

US 2018/0252640 A1   Sep. 6, 2018

(51) Int. Cl.
*G01N 21/61* (2006.01)
*G01N 33/00* (2006.01)
*G01N 21/3504* (2014.01)
*G01N 21/3518* (2014.01)

(52) U.S. Cl.
CPC ..... *G01N 21/3518* (2013.01); *G01N 21/3504* (2013.01); *G01N 33/0032* (2013.01); *G01N 21/61* (2013.01); *G01N 2201/1218* (2013.01)

(58) Field of Classification Search
CPC .................................................. G01N 21/3518
See application file for complete search history.

(56) References Cited

U.S. PATENT DOCUMENTS

| 4,010,717 | A |   | 3/1977  | Taplin |
|-----------|---|---|---------|--------|
| 4,355,280 | A |   | 10/1982 | Duzich |
| 4,383,840 | A | * | 5/1983  | Jones ............ B01D 46/0075 55/283 |
| 5,343,755 | A |   | 9/1994  | Huss   |
| 5,349,347 | A |   | 9/1994  | Muller |
| 5,362,967 | A | * | 11/1994 | Aoki .................. G01N 21/37 250/343 |

(Continued)

FOREIGN PATENT DOCUMENTS

| CN | 104964790 A | 10/2015 |
|----|-------------|---------|
| EP | 0834733 A2  | 4/1998  |

(Continued)

OTHER PUBLICATIONS

CO2 Measurement in Incubators—Questions and Answers; Vaisala Application Note_Sep. 2009.

(Continued)

*Primary Examiner* — David P Porta
*Assistant Examiner* — Jeremy S Valentiner
(74) *Attorney, Agent, or Firm* — Shimokaji IP

(57) ABSTRACT

Apparatus for determining concentration of a targeted gas in environmental air, the apparatus includes a non-dispersive infrared (NDIR) sensor, a pressure sensor coupled in fluid communication with an interior of the NDIR sensor; and a processor. The processor is configured to receive pressure data from the pressure sensor based on gas pressure within an interior of the NDIR sensor, receive a target-gas concentration signal from the NDIR sensor, and produce a pressure-compensated concentration signal based on the target-gas concentration signal, a predetermined reference pressure and the pressure data from the pressure sensor.

17 Claims, 2 Drawing Sheets

(56) References Cited

U.S. PATENT DOCUMENTS

| | | |
|---|---|---|
| 5,747,808 A | 5/1998 | Engelhard |
| 6,016,702 A | 1/2000 | Maron |
| 6,619,141 B2 | 9/2003 | Soren |
| 8,199,200 B2 | 6/2012 | Kawai et al. |
| 8,912,852 B2 | 12/2014 | Godager |
| 9,222,912 B2 | 12/2015 | Diehl et al. |
| 9,228,524 B2 | 1/2016 | Song |
| 2005/0088563 A1 | 4/2005 | Junichi et al. |
| 2006/0177362 A1* | 8/2006 | D'Evelyn ............ B01J 3/002 422/245.1 |
| 2007/0137150 A1 | 6/2007 | Catepillar |
| 2010/0110437 A1* | 5/2010 | Furtaw ............... G01K 13/02 356/437 |
| 2012/0078532 A1* | 3/2012 | Forsyth ............ G01N 21/274 702/24 |
| 2014/0166910 A1 | 6/2014 | Endress |
| 2015/0020599 A1 | 1/2015 | Pechstedt et al. |
| 2016/0077072 A1 | 3/2016 | Tsuzuki et al. |
| 2016/0091472 A1* | 3/2016 | Moenkemoeller ............ G01N 33/0006 73/114.71 |
| 2017/0074458 A1* | 3/2017 | Handa ................ F17C 13/084 |
| 2018/0202920 A1* | 7/2018 | Borgen ............... G01N 21/15 |

FOREIGN PATENT DOCUMENTS

| | | |
|---|---|---|
| JP | H11201511 A | 7/1999 |
| TW | M471585 | 2/2014 |

OTHER PUBLICATIONS

Effects of Temperature and Barometric Pressure on CO2 Sensors—Application Note—Building Automation Products, Inc.—Jan. 25, 2017.

Gaynullin et al., "A Practical Solution for Accurate Studies of NDIR Gas Sensor Pressure Dependence," 2016 IEEE Sensors, IEEE, Oct. 30, 2016, 1-3.

Frodl et al., "An Automotive Bi-Source Spectroscopic Carbon Dioxide Sensor with Pressure Compensation," Sensors and Actuators B 127 (2007) 82-88.

EP Search, Application No. 18159609.9-1020, dated May 28, 2018.

\* cited by examiner

GAS CONCENTRATION SENSOR WITH IMPROVED ACCURACY

BACKGROUND OF THE INVENTION

The present invention generally relates to sensors for determining concentration of particular gas in a gas mixture. More particularly, the present invention relates to improving accuracy of non-dispersive infrared (NDIR) sensors in a gaseous environment, such as air, subject to dynamic pressure variation.

The size of a typical NDIR sampling chamber is fixed and is open to the atmosphere so that air can move in and out. The number of air molecules in a given volume is affected by temperature and air pressure but not the concentration of a target gas such as CO2. At low pressures or high temperatures, there will be fewer air molecules in the sample chamber, so there will also be fewer CO2 molecules, even though the parts per million (ppm) of CO2 hasn't changed. Fewer CO2 molecules "fools" the sensor into thinking that the CO2 concentration is lower than it really is. At high pressures or low temperatures, there are more air molecules in the sample chamber and more CO2 molecules, even though the CO2 concentration hasn't changed. More CO2 molecules "fools" the sensor into thinking that the CO2 concentration is higher than it really is. Therefore a CO2 sensor calibration will only be accurate at one temperature and one air pressure.

Typically, NDIR sensors are connected to output devices or displays with intervening pressure and temperature compensation devices. Such prior art pressure compensation devices employ correction factors based on the Ideal Gas Law as follows:

$$\text{ppm CO2 corrected} = \text{ppm CO2 measured} * ((T_{measured} * p_{ref})/(p_{measured} * T_{ref})) \quad (1)$$

where pmeasured=Current pressure; Tref=reference temperature; Tmeasured=Current absolute temperature; and pref=reference Barometric Pressure.

This system for pressure and temperature compensation has been found to be effective when applied to variations of atmospheric conditions which occur at a relatively slow rate. For example, when atmospheric pressure and temperature may change over a period of 12 hours or more as weather conditions change.

However, when there is a rapid change of ambient pressure of the environment in which the NDIR sensor is employed, the prior-art system of compensation may not be fully effective. For example, if an NDIR sensor were employed in an aircraft, cabin pressure in the aircraft might change in a matter of minutes as the aircraft climbs or descends. Similarly, if an NDIR sensor were employed in a land-based vehicle, the sensor may be exposed to varying pressures as the vehicle travels up or down mountainous terrain. Under such dynamically varying conditions, compensation based only on application of the Ideal Gas Law may not be sufficient to assure accurate results from the NDIR sensor.

In a typical vehicular installation of an NDIR sensor, a diffusion filter may be placed over an opening of the sensor to prevent entry of contaminants into the sensor. With the passage of time, the diffusion filter may become dirty. As the diffusion filter become increasing dirty, the rate of air flow into the sensor may diminish. As a result, the sensor may become increasingly insensitive to dynamic variations of atmospheric pressure and overall accuracy of the sensor may be correspondingly diminished.

As can be seen, there is a need for an NDIR sensor that may provide accurate gas concentration data even when operating in an environment subject to dynamic pressure changes. More particularly, there is a need for a system of compensating for pressure and temperature changes when such a sensor is incorporated in a vehicle. Still further, there is a need to prevent sensor insensitivity arising from progressive clogging of diffusion filters of NDIR sensors.

SUMMARY OF THE INVENTION

In one aspect of the present invention, apparatus for determining concentration of a targeted gas in environmental air, the apparatus comprises: a non-dispersive infrared (NDIR) sensor; a pressure sensor coupled in fluid communication with an interior of the NDIR sensor; and a processor configured to; receive pressure data from the pressure sensor based on gas pressure within an interior of the NDIR sensor; receive a target-gas concentration signal from the NDIR sensor, and produce a pressure-compensated concentration signal based on the target-gas concentration signal, a predetermined reference pressure and the pressure data from the pressure sensor.

In another aspect of the present invention, a self-cleaning non-dispersive infrared (NDIR) sensor comprises: a pressure sensor coupled in fluid communication with an interior of the NDIR sensor and in fluid communication with an exterior of the NDIR sensor; and a vibratory device coupled to a diffusion filter of the NDIR sensor; wherein the vibratory device is configured to vibrate the diffusion filter responsively to development of a threshold air pressure differential between the exterior and the interior of the NDIR sensor.

In still another aspect of the present invention, apparatus for sensing concentration of a target gas in air comprises: a non-dispersive infrared (NDIR) sensor; a housing surrounding the NDIR sensor; an air inlet port in fluid communication with the housing; an air outlet port in fluid communication with the housing; a divider interposed between the air inlet port and the air outlet port; and a thermoelectric heat pump embedded in the divider for producing an air pressure differential between air in the air inlet port and air in the outlet port.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a non-dispersive infrared detection (NDIR) sensor unit which provides accurate target-gas concentration data in an environment subject to dynamic pressure changes. More particularly, there is provided a system of compensating for pressure and temperature changes when such a sensor unit is installed in a vehicle. Still further, there is a provided a system to prevent sensor insensitivity arising from progressive clogging of diffusion filters of NDIR sensors employed in such sensor units.

Figure 1:
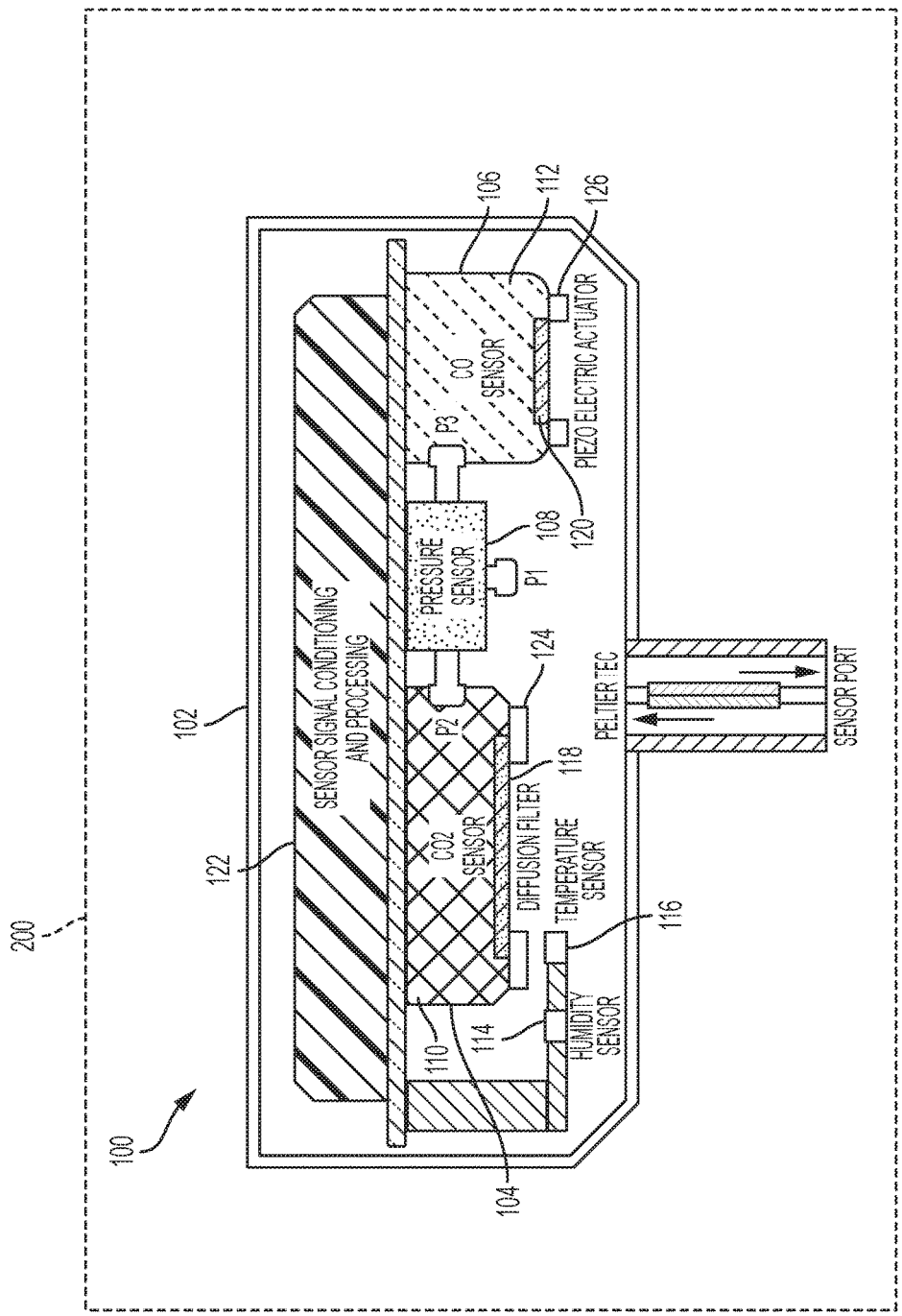
FIG. 1 is a cross-sectional schematic view of a gas concentration sensing unit in accordance with an exemplary embodiment of the invention.

Referring now to FIG. 1, an exemplary embodiment of target-gas concentration sensing unit 100 may comprise a housing 102 and one of more non-dispersive infrared (NDIR) sensors 104 and 106. In an exemplary embodiment, the sensor 104 may be configured to measure a concentration of carbon dioxide ($CO_2$) and the sensor 106 may be configured to measure a concentration of carbon monoxide (CO). A pressure sensor 108 may be connected in fluid communication with an interior 110 of the sensor 104 and/or an interior 112 of the sensor 106. The pressure sensor 108 may be configured to measure pressure P2 within the interior 110 and/or pressure P3 within the interior 112. The sensing unit 100 may also include a humidity sensor 114 and a temperature sensor 116.

In an exemplary embodiment, the sensing unit 100 may be installed in a vehicle 200, such as an aircraft or a ground-based vehicle. The pressure sensor 108 may be configured to measure pressure, P1, external to the sensors 104 and 106 but internal to the housing 102. In that regard, the pressure sensors may be considered capable of measuring atmospheric pressure within the vehicle 200.

The sensors 104 and 106 may be provided with diffusion filters 118 and 120 which may block entry of contaminants, such as dust, into the interiors 110 and 112 of the sensors 104 and 106. It may be noted that the vehicle 200 may move from one altitude to another within a matter of minutes. As a consequence, there may be a dynamic variation of the pressure P1. Presence of the diffusion filters 118 and 120 may result in development of a pressure differential between the pressure P1 and the pressures P2 and/or P3.

The NDIR sensors 104 and 106 may be initially calibrated to determine concentration of a target gas at a reference pressure, Pref, and a reference temperature, Tref, for example, sea level pressure and 25 degrees C. temperature. When atmospheric conditions surrounding the typical NDIR sensor depart from the Pref and Tref, there is need to conduct a compensation operation in an attempt to derive accurate data from the sensor.

Such compensation is difficult to perform if the sensor unit 100 is installed in a vehicle because the unit 100 may be exposed to a rapid change in atmospheric pressure as the vehicle 200 changes altitude. Consequently, there may arise numerous circumstances in which P2 and/or P3 differ from P1 and also differ from Pref.

In accordance with an exemplary embodiment of the invention, accuracy of the sensing unit 100 may be achieved by applying an effective compensation correction factor to raw data emerging from the NDIR sensors 104 and/or 106. Additionally, accuracy may be achieved by monitoring the cleanliness of the diffusion filters 118 and/or 120 and cleaning the filters whenever a threshold level of cleanliness is not met. Still further enhancement of accuracy may be achieved by providing for a positive circulating flow of air into and out of the housing 102 of the sensing unit 100.

As to the first technique for attaining accuracy, the sensing unit 100 may be provided with a processor 122. The processor 122 may be interconnected the temperature sensor 116 to receive temperature signals and with the pressure sensor 108 to receive pressure signals corresponding to values of P2 and/or P3. The processor 122 may be interconnected with a non-volatile memory (not shown) in which a compensation transfer function may be stored. In an exemplary embodiment, the transfer function may be characterized as follows:

$$\rho_{compensated} = \frac{\rho_{measured} P_{ref}^2 (T + 273K)}{298K \; P^2} \qquad (2)$$

Where;
$\rho$=CO2 or CO concentration(PPM)
P=Pressure (P2) or (P3) inside the sensor (hPa)
$P_{ref}$=Reference Pressure at sea level 1013.25 (hPa)
T=Temperature of the sensor (deg C)

It may be noted that the above described transfer function differs from prior art correction factors which are based on the Ideal Gas Law. In prior art correction factors, a corrected concentration of a target gas is derived from a linear relationship of reference pressure and measured pressure as in prior-art equation (1) above. In equation (2) above, unlike the prior art, compensated concentration is derived from a reference pressure squared and a measured pressure squared. In other words, the transfer function is based on a unique second order relationship of reference pressure, Pref, and measured pressure, P2 or P3.

When the transfer function of equation (2) is employed to calculate a compensated concentration of a target gas, the actual concentration of the target gas may be accurately determined on a continuous basis, even though the NDIR sensor 104 or 106 may be subjected to dynamically varying pressure changes. In other words, even though there may be rapidly varying altitude changes of a vehicle 200 in which the sensor 104 and/or 106 is installed, the sensor unit 100 may continuously provide accurate target-gas concentration data.

Referring again to FIG. 1, there is shown an exemplary embodiment of another system which may be employed to enhance accuracy of the NDIR sensors 104 and 106. Vibratory devices such as Piezo-electric rings 124 and 126 may be positioned near outer edges of the diffusion filters 118 and 120 respectively. The piezo-electric rings 124 and 126 may be interconnected with the processor 122, the pressure sensor 108 and the humidity sensor 114. In operation, the rings 124 and 126 may be activated to vibrate the diffusion filters 118 and 120 in order to shake dust out of the filters. Activation of the rings 124 and 126 may occur when a pressure differential between the pressure P1 and the pressure P2 and/or P3 exceeds a predetermined threshold. The rings 124 and 126 may vibrate continuously until the pressure differential P2 or P3 minus P1 is reduced to a level equal to or less than the predetermined threshold level. Even in the presence of a pressure differential that may exceed the threshold, vibration of the rings may be delayed until relative humidity in the housing 102 may be equal to or less than 20% as determined by the humidity sensor 114.

Figure 2:
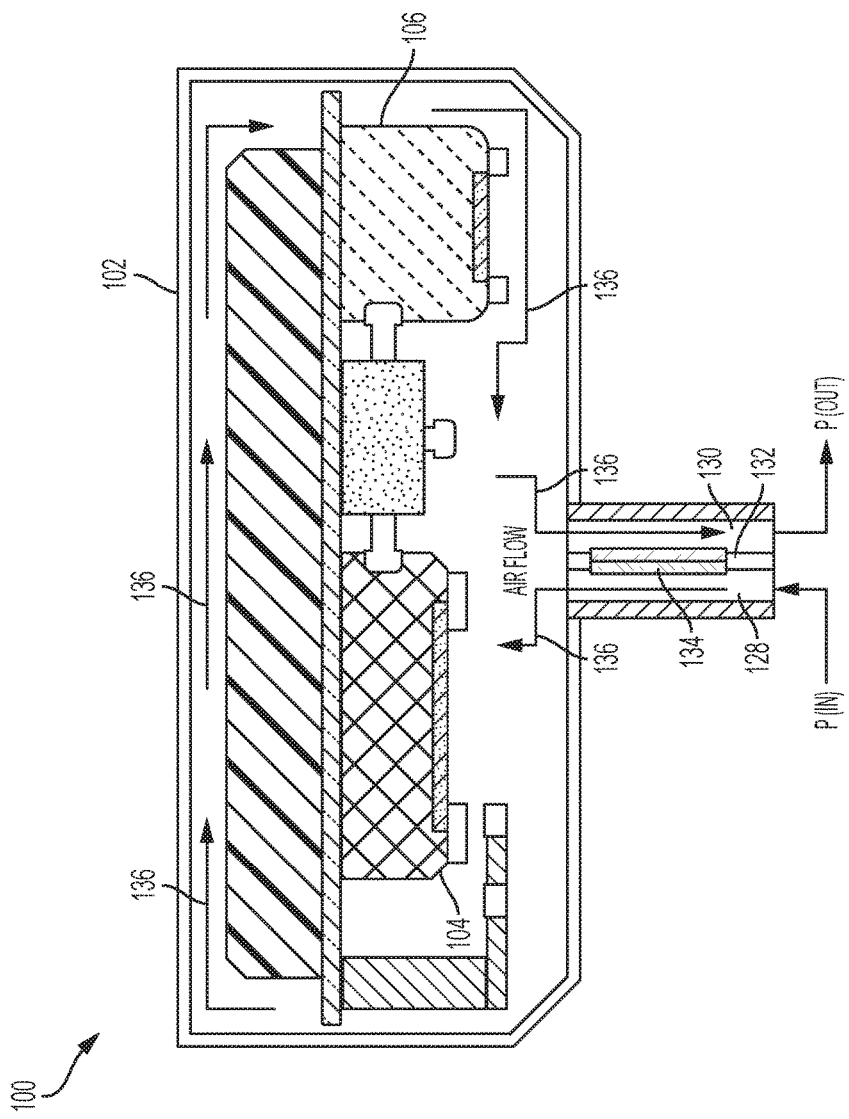
FIG. 2 is a simplified cross-sectional schematic view of a gas concentration sensing unit of FIG. 1 accordance with an exemplary embodiment of the invention.

Referring now to FIG. 2 there is shown still another exemplary embodiment of the invention which may be employed to enhance accuracy of the NDIR sensors 104 and 106. The housing 102 may be provided with an air inlet port 128 and an air outlet port 130. The ports 128 and 130 may be positioned adjacent to one another with a divider 132 interposed between them. A thermoelectric heat pump 134 may be embedded in the divider 132. The heat pump 134 may create heat flux between p-n junctions of an array of solid-state active materials. Consequently, the heat pump 134 may generate an air pressure differential, i.e., [P(out)−P(in)] between the air outlet port 130 and the air inlet port 128. This air pressure differential may produce positive air flow in the ports 128 and 130 and a circulating air flow 136 within the housing 102 of the sensing unit 100. As a result of the circulating air flow 136, the NDIR sensors 104 and 106 may be supplied with fresh atmospheric air that is representative of actual air conditions in the vehicle 200 in which the sensors 104 and 106 may be installed.

It should be understood, of course, that the foregoing relates to exemplary embodiments of the invention and that modifications may be made without departing from the spirit and scope of the invention as set forth in the following claims.

We claim:

1. An apparatus for determining concentration of a target gas in an environmental air, the apparatus comprising:
    a housing in the environmental air;
    a non-dispersive infrared (NDIR) sensor in the housing;
    a pressure sensor in the housing and in fluid communication with an interior of the NDIR sensor;
    a diffusion filter positioned on the NDIR sensor;
    a vibratory device surrounding the diffusion filter;
    wherein the vibratory device is configured to vibrate the diffusion filter responsively to development of a threshold pressure differential between a pressure exterior of and a pressure interior of the NDIR sensor;
    wherein the vibratory device is configured to vibrate the diffusion filter only when relative humidity is lower than 20% interiorly of the housing and exteriorly of the NDIR sensor; and
    a processor configured to:
        receive pressure data from the pressure sensor based on total pressure within the interior of the NDIR sensor;
        receive a target gas concentration signal from the NDIR sensor, and
        produce a pressure-compensated concentration signal based on the target gas concentration signal, a predetermined reference pressure of the environmental air, and the pressure data from the pressure sensor.

2. The apparatus of claim 1 wherein the processor is configured to receive temperature data based on temperature interiorly of the housing and exteriorly of the sensor.

3. The apparatus of claim 1 wherein the pressure-compensated concentration signal is based, at least in part, on a value of the predetermined reference pressure squared and a value of the pressure data from the pressure sensor squared.

4. The apparatus of claim 1 wherein the processor produces the pressure-compensated signal by employing a transfer function formulated as:

$$\rho_{compensated} = \frac{\rho_{measured} P_{ref}^2 (T + 273K)}{298K\ P^2}$$

wherein:
    ρ=target gas concentration (PPM)
    P=Pressure inside the sensor (hPa)
    $P_{ref}$=Reference Pressure at sea level 1013.25 (hPa)
    T=Temperature within the housing but outside of the sensor (deg C).

5. The apparatus of claim 1 wherein the NDIR sensor is configured to be installed in a vehicle.

6. The apparatus of claim 1 wherein the vibratory device is a piezo-electric actuator.

7. The apparatus of claim 1 further comprising:
    an enclosure surrounding the NDIR sensor;
    an inlet to the enclosure;
    an outlet to the enclosure; and
    an air-flow producing device interposed between the inlet and the outlet to produce circulating air flow through the enclosure.

8. The apparatus of claim 7 wherein the air-flow producing device is a thermoelectric heat pump.

9. A non-dispersive infrared (NDIR) sensor, comprising:
    a pressure sensor configured to measure an internal pressure within the NDIR sensor, as well as an external pressure outside of the NDIR sensor within an interior of a housing surrounding the NDIR sensor and the pressure sensor; and
    a vibratory device coupled to a diffusion filter of the NDIR sensor;
    wherein the vibratory device is configured to vibrate the diffusion filter responsively to development of a threshold air pressure differential between the exterior and the interior of the NDIR sensor.

10. The NDIR sensor of claim 9 wherein the vibratory device is configured to vibrate continuously after development of the threshold air pressure differential until the air pressure differential is at or below the threshold air pressure differential.

11. The NDIR sensor of claim 9 wherein the vibratory device is a piezo-electric actuator.

12. The NDIR sensor of claim 9 wherein the vibratory device is configured to vibrate the diffusion filter only when relative humidity is lower than 20% in an atmosphere surrounding the NDIR sensor.

13. The NDIR sensor of claim 9:
    wherein the sensor is installed in a housing of a sensing unit, and
    wherein the sensing unit is configured to be installed in a vehicle.

14. An apparatus for sensing concentration of a target gas in an environmental air comprising:
    a non-dispersive infrared (NDIR) sensor;
    a housing surrounding the NDIR sensor;
    a pressure sensor in the housing, wherein the pressure sensor is configured to measure an internal pressure within the NDIR sensor, as well as an external pressure outside of the NDIR sensor within an interior of the housing;
    an inlet port configured to allow environmental air to flow into the interior of the housing;
    an outlet port configured to allow interior housing air to flow out of the interior of the housing;
    a divider interposed between the inlet port and the outlet port; and
    a thermoelectric heat pump embedded in the divider for producing a pressure differential between the air inlet port and the outlet port.

15. The apparatus of claim 14 wherein the inlet port and the outlet port are positioned adjacent to one another.

16. The apparatus of claim 14 wherein the pressure differential produces a circulating air flow through the housing and around the NDIR sensor.

17. The apparatus of claim 14 wherein the housing is configured to be installed in a vehicle.

\* \* \* \* \*